(12) United States Patent
Stan

(10) Patent No.: US 11,389,261 B2
(45) Date of Patent: Jul. 19, 2022

(54) CLIPPING DEVICE

(71) Applicant: Eastern Currents Ltd., Vancouver (CA)

(72) Inventor: John Dumitru Stan, Vancouver (CA)

(73) Assignee: Eastern Currents Ltd., Vancouver (CA)

( * ) Notice: Subject to any disclaimer, the term of this patent is extended or adjusted under 35 U.S.C. 154(b) by 108 days.

(21) Appl. No.: 17/020,648

(22) Filed: Sep. 14, 2020

(65) Prior Publication Data

US 2021/0077214 A1 Mar. 18, 2021

Related U.S. Application Data

(60) Provisional application No. 62/899,902, filed on Sep. 13, 2019.

(51) Int. Cl.
| | |
|---|---|
| *A47G 1/17* | (2006.01) |
| *A61B 50/20* | (2016.01) |
| *A61H 39/08* | (2006.01) |
| *F16B 2/10* | (2006.01) |
| *A61B 50/30* | (2016.01) |
| *A61B 50/00* | (2016.01) |

(52) U.S. Cl.
CPC .......... *A61B 50/20* (2016.02); *A61B 50/3001* (2016.02); *A61H 39/086* (2013.01); *F16B 2/10* (2013.01); *A61B 2050/0053* (2016.02); *A61B 2050/21* (2016.02)

(58) Field of Classification Search
CPC ............ A61B 50/20; A61B 2050/0053; A61B 2050/21; A61B 50/3001; F16B 2/10; A61H 39/086
USPC ............. 248/206.5, 683, 316.1, 316.7, 309.4
See application file for complete search history.

(56) References Cited

U.S. PATENT DOCUMENTS

| | | | |
|---|---|---|---|
| 9,577,417 B2* | 2/2017 | Stechmann | ............... F16B 1/00 |
| 10,627,043 B2* | 4/2020 | Wargo | ...................... H01Q 1/12 |
| 11,162,633 B2* | 11/2021 | Sullivan | ................... H01F 7/02 |
| 2017/0159880 A1* | 6/2017 | Stechmann | ............... F16B 1/00 |

* cited by examiner

*Primary Examiner* — Todd M Epps
(74) *Attorney, Agent, or Firm* — McMillan LLP

(57) ABSTRACT

This disclosure describes a device comprising: (a) a first component for providing a means for securing acupuncture needles that are disposed in bulk-style packaging when such bulk-style package is opened; and (b) a second component for providing a mounting and resting surface for the first component. The first component and the second component may be coupled together by a coupling mechanism disposed therebetween. The device may permit an acupuncture practitioner to remove an acupuncture needle from bulk packaging, without accidentally touching the shaft of an adjacent or another acupuncture needle contained within the same bulk packaging, or accidentally spilling needles in an open package while moving packaging around during treatment.

8 Claims, 9 Drawing Sheets

CLIPPING DEVICE

TECHNICAL FIELD

The present disclosure relates to a clipping and mounting device and use thereof. The present disclosure also relates to a clipping and mounting device for use in the acupuncture industry.

BACKGROUND

Acupuncture needles are generally packaged individually (tubed or un-tubed versions) or together in bulk packaging. Bulk packaging varieties include, but are not limited to, "blister" style packaging (either with a paper back or foil back or other suitable backing) and plastic "pouch" packaging. Owing to at least environmental concerns, and perhaps packaging cost concerns, the acupuncture industry has in recent years been moving more towards bulk packaging; and presently, it is not uncommon for 5, 10, or 20 acupuncture needles to be packaged together with one or more guide tubes included in the packaging. Plastic insertion tubes may also be packaged separately from needles, and such empty tubes may also be bulk packaged in groups of 5, 10, or 20 per package. Unfortunately, acupuncture needles are generally loose in bulk-style packaging and it is not uncommon for such acupuncture needles to fall out from such packaging or for a practitioner to inadvertently touch the shaft of more than one needle in an attempt to retrieve the handle of only one needle from the packaging. In addition, bulk packages generally lack resealable openings and therefore have no immediate method for re-sealing the package so as to keep the needles that are not removed from the bulk package within a protected environment. Moreover and once opened, bulk packaged needles have no convenient, clean, mobile surface to be mounted on while the needles are being accessed by a acupuncturist during treatment.

SUMMARY

According to a part of the disclosure, there is a device comprising: (a) a first component, the first component comprising: (i) a first layer comprising a first surface and a second surface opposite the first surface, the second surface comprising a first magnetic material; (ii) a second layer comprising a first surface and a second surface opposite the first surface, the second surface comprising a second magnetic material. The second surface of the first component and the second surface of the second component are adapted for creating an attractive magnetic force therebetween when the second surface of the first component and the second surface of the second component are proximate to each other in an overlapping arrangement.

The first layer and the second layer of the first component may be coupled to each other in a manner to permit the first component to reversibly transition between an opened position and a closed position.

The first magnetic material may be selected from a group consisting of ceramic magnets, ferrite magnets, magnets comprising neodymium, and any combination thereof. The second magnetic material may be selected from a group consisting of ceramic magnets, ferrite magnets, magnets comprising neodymium, and any combination thereof.

The second layer may be longer than the first layer such that when the first layer overlaps with the second layer, a lip is created.

According to another part of the disclosure, there is a device comprising a first component and a second component. The second component comprises: (i) a first layer comprising a first surface and a second surface opposite the first surface, the second surface comprising a deformable material; (ii) a second layer comprising a first surface and a second surface opposite the first surface, the second surface comprising a deformable material; (iii) a locking mechanism for reversibly coupling the first layer and the second layer of the second component together in a manner where the second surface of the first layer and the second surface of the second layer are proximate and facing towards each other.

The locking mechanism may comprise: (a) a first part with an aperture extending therethrough and extending from an edge of the first layer; and (b) a second part that forms a protrusion extending from an edge of the second layer, the second part adapted to extend through the aperture of the first part.

The edges surrounding the aperture of the first part of the locking mechanism may be serrated. The edges of the second part of the locking mechanism may be serrated. The edges of the aperture and the edges of the second part may inter-lock when the second part extends through the aperture of the first part. The length of the second part extending through the aperture of the first part may be correlated to a magnitude of force exerted between the deformable materials of the first layer and the second layer of the second component, when such deformable materials overlap each other.

The second component may further comprise a first extension that extends in a direction that is away from the first surface of the second layer. The first part of the locking mechanism may serve as a complementary extension to the first extension so as to elevate the first surface of the second component off a surface, when the locking mechanism is in a locked position.

According to another part of the disclosure, there is a device comprising a first component and a second component. The second component comprises a first portion, a plurality of extensions extending away from the first portion, and one or more holders each for receiving a needle tube. The second component is adapted to couple to the first component. The first component and the second component may be coupled together by magnetic means.

According to another part of the disclosure, the device may further comprise a coupling mechanism disposed between (i) the first surface of the second layer of the first component and (ii) the first surface of the first layer of the second component, the coupling mechanism for coupling the first component and the second component together.

The coupling mechanism may be a magnetic mechanism.

According to another part of the disclosure, the device may be used for an application of acupuncture needles into a subject.

The device disclosed herein may provide a means for securing acupuncture needles that are disposed in bulk-style packaging when such bulk-style package is opened.

The device disclosed herein may provide a means for securing acupuncture needle insertion tubes that are disposed in bulk-style packaging when such bulk-style package is opened.

The device disclosed herein may provide a means for a practitioner to retrieve one needle from bulk packaging at a time, while reducing the likelihood that such practitioner will touch the shaft of more than one needle in said bulk packaging during the process of removing the handle and shaft of said one needle from said bulk packaging, thereby contaminating said more than one needle.

The device disclosed herein may provide a means for a practitioner to retrieve one needle from bulk packaging at a time, while reducing the likelihood of spilling the needles within the bulk packaging in the process of retrieving such one needle.

The device disclosed herein may provide a means for a practitioner to manoeuvre a bulk package of needles on a surface.

The device disclosed herein may provide a means for a practitioner to elevate acupuncture needles above a potentially contaminated surface.

The device disclosed herein may provide a means for re-sealing an opened bulk package.

According to another part of the disclosure, there is a supporting base comprising: (a) a first portion comprising a first surface and a second surface that is opposite the first surface, the first portion further comprising a plurality of edges circumscribing at least the first surface, the plurality of edges including a first edge and a second edge that is opposite the first edge; (b) a magnetic layer coupled to the first surface of the first portion; (c) a first support extending away from the first edge, the first support comprising a portion that serves as a first foot; (d) a second support extending away from the second edge, the second support comprising a portion that serves as a second foot; wherein the first support, the second support, and the second surface of the first portion form a channel; wherein the first foot comprises a holder that is configured to receive a longitudinal tube; wherein the magnetic layer coupled to the first surface of the first portion is configured to couple to a first component through magnetic attraction; and wherein the supporting base is configured to support a mass of the first component.

The magnetic layer may be selected from a group consisting of ceramic magnets, ferrite magnets, magnets comprising neodymium, and any combination thereof.

According to another part of the disclosure, there is a device comprising: (a) a first component, the first component comprising: (i) a first layer comprising a first surface and a second surface opposite the first surface, the second surface comprising a first magnetic material; (ii) a second layer comprising a first surface and a second surface opposite the first surface, the second surface comprising a second magnetic material; and (b) a supporting base comprising: (a) a first portion comprising a first surface and a second surface that is opposite the first surface, the first portion further comprising a plurality of edges circumscribing at least the first surface, the plurality of edges including a first edge and a second edge that is opposite the first edge; (b) a magnetic layer coupled to the first surface of the first portion; (c) a first support extending away from the first edge, the first support comprising a portion that serves as a first foot; (d) a second support extending away from the second edge, the second support comprising a portion that serves as a second foot; wherein the first support, the second support, and the second surface of the first portion form a channel; wherein the first foot comprises a holder that is configured to receive a longitudinal tube; wherein the magnetic layer coupled to the first surface of the first portion is configured to couple to a first component through magnetic attraction; and wherein the supporting base is configured to support a mass of the first component; the second magnetic material of the first component and the magnetic layer of the supporting base being configured to create an attractive magnetic force therebetween when the second magnetic material of the first component and the magnetic layer of the supporting base are proximate to each other and in an overlapping arrangement.

This summary does not necessarily describe the entire scope of all aspects of the disclosure. Other aspects, features and advantages will be apparent to those of ordinary skill in the art upon review of the following description of specific embodiments.

BRIEF DESCRIPTION OF THE DRAWINGS

In the accompanying drawings, which illustrate one or more embodiments.

DETAILED DESCRIPTION

Figure 1A:
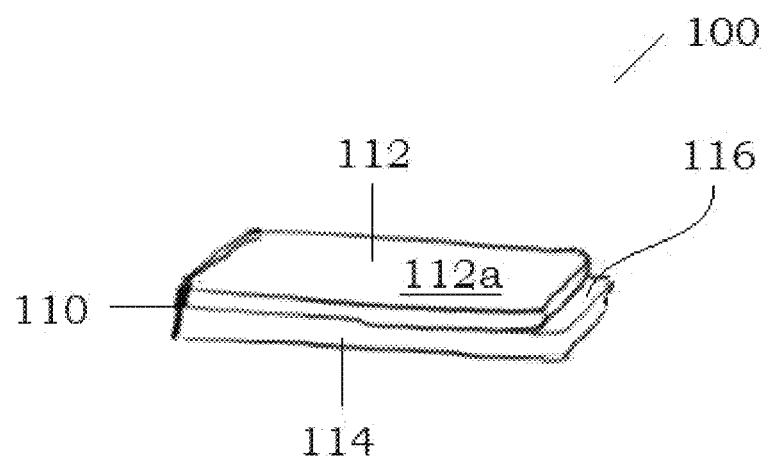
FIG. 1(a) is a perspective view of a clipping device, the clipping device being depicted in its "closed" position where a first layer of the clipping device is in overlapping arrangement with a second layer of the clipping device.

Directional terms such as "top," "bottom," "upwards," "downwards," "vertically," and "laterally" are used in the following description for the purpose of providing relative reference only, and are not intended to suggest any limitations on how any article is to be positioned during use, or to be mounted in an assembly or relative to an environment. The use of the word "a" or "an" when used herein in conjunction with the term "comprising" may mean "one," but it is also consistent with the meaning of "one or more," "at least one" and "one or more than one." Any element expressed in the singular form also encompasses its plural form. Any element expressed in the plural form also encompasses its singular form. The term "plurality" as used herein means more than one; for example, the term "plurality includes two or more, three or more, four or more, or the like.

In this disclosure, the terms "comprising", "having", "including", and "containing", and grammatical variations thereof, are inclusive or open-ended and do not exclude additional, un-recited elements and/or method steps. The term "consisting essentially of" when used herein in connection with a composition, use or method, denotes that additional elements, method steps or both additional elements and method steps may be present, but that these additions do not materially affect the manner in which the recited composition, method, or use functions. The term "consisting of" when used herein in connection with a composition, use, or method, excludes the presence of additional elements and/or method steps.

As used in this disclosure, the term "about", when used to describe a value, means within 5% of the stated value.

As used in this disclosure, the term "closed position" means a position where the first layer and the second layer of a component are held in place (e.g. by means of attractive forces or locking mechanism) relative to each other, and where at least a portion of the first layer and a portion of the second layer of the component overlap.

As used in this disclosure, the term "couplability" refers to the ability of two or more coupled items to remain coupled to one another, or the likelihood that two or more items will remain coupled together.

As used in this disclosure, the term "opened position" means a position where the first layer and the second layer of a component do not overlap.

As used in this disclosure, the term "substantially" is intended to contemplate any and all variations or deviations that are not of material effect.

The present disclosure relates to a clipping device and use thereof. The clipping device can provide a means for controlling the size of an opening of a bulk packaging, the bulk packaging containing one or more acupuncture needles therein. The clipping device can provide a means for reducing the likelihood of contamination of acupuncture needles that remain in opened packaging, as acupuncture needles are removed from the open packaging over time. The clipping device can provide a means for keeping acupuncture needles elevated above a surface. The clipping device can provide a means for reducing the time that it takes a practitioner to retrieve an acupuncture needle from a bulk package of acupuncture needles. The clipping device can provide a means for securing acupuncture needles that are disposed in bulk-style packaging when such bulk-style package is opened.

Clipping Device

Figure 1B:
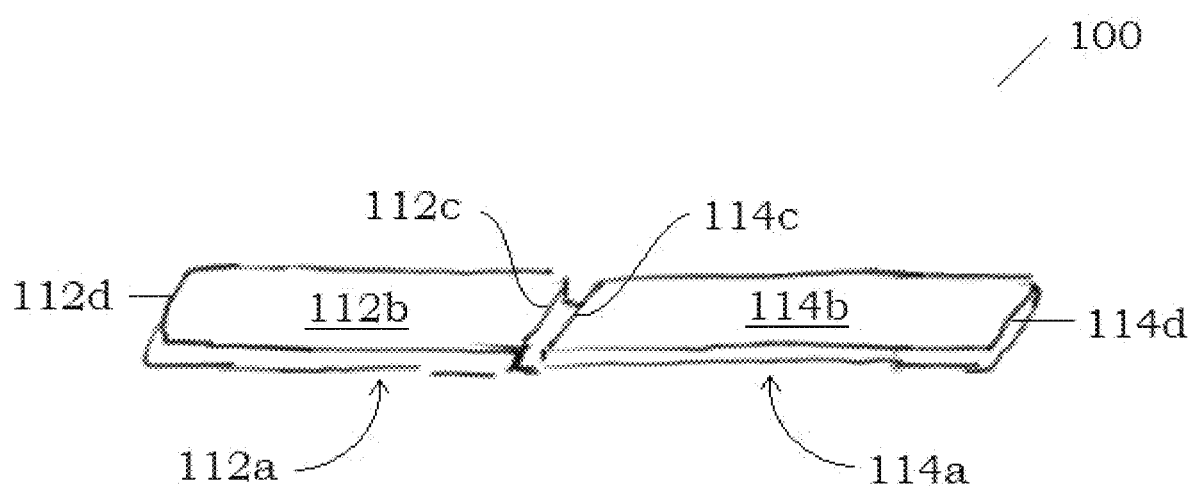
FIG. 1(b) is a perspective view of the clipping device depicted in FIG. 1(a), the clipping device being depicted in an "opened" position.

Referring to FIGS. 1(a) and 1(b), and according to an embodiment of a clipping device, there is a clipping device 100. The clipping device 100 comprises a first component 110. First component 110 has a first layer 112 and a second layer 114.

The first layer 112 comprises a first surface 112a, and a second surface 112b that is opposite the first surface 112a. The first layer 112 also comprises a first edge 112c and a second edge 112d that is opposite the first edge 112c. The second layer 114 comprises a first surface 114a, and a second surface 114b that is opposite the first surface 114a. The second layer 114 also comprises a first edge 114c and a second edge 114d that is opposite the first edge 114c. First layer 112 and second layer 114 are coupled to each other at edges 112c and 114c by a hinge mechanism, the hinge mechanism for permitting first layer 112 to overlap with second layer 114 and for allowing the clipping device 100 to reversibly transition from an "opened" position to a "closed" position.

The first layer 112 and the second layer 114 each comprise a magnetic material, such that an attractive magnetic force is created between the surface 112b and surface 114b when surface 112b and surface 114b are proximate to each other and arranged relative to each other in an overlapping manner. The magnetic material may be any suitable magnetic material known in the art such as but not limited to permanent magnets, temporary magnets, ceramic magnets, ferrite magnets, magnets comprising neodymium.

The first component 110 is adapted for receiving an object (e.g. an opened bulk package containing acupuncture needles therein) between surface 112b and surface 114b. As contemplated in this embodiment, first component 110 is adapted for receiving bulk packaged needles that are packaged in a pouch pack style. When the object is received between surface 112b and surface 114b, the attractive magnetic force created by placing surface 112b and surface 114b proximate to each other in overlapping arrangement restricts the ability of the object (and any other removable or loose articles therein or thereon) to move relative to the first component 110, but is not so strong so that any removable or loose articles (e.g. acupuncture needles) in or on the object (e.g. bulk packaging) cannot be removed from between surface 112b and surface 114b upon application of a pulling force that is applied substantially perpendicular to the direction of the attractive magnetic force between surface 112b and surface 114b. As contemplated in this embodiment, the attractive magnetic force created by placing surface 112b and surface 114b proximate to each other in overlapping arrangement correlates to a pressure on the object that ranges between about 0.7 psi and about 10 psi. For example, the pressure exerted on an object disposed between surface 112b and surface 114b as a result of the attractive magnetic force created by placing surface 112b and surface 114b can range from about 0.7 psi to about 8 psi, about 0.7 psi to about 6 psi, about 1.5 psi to about 5 psi, about 2 psi to about 4 psi. For example, the psi can be 0.7, 1.0, 1.2, 1.4, 1.6, 1.8, 2.0, 2.2, 2.4, 2.6, 2.8, 3.0, 3.5, 4.0, 4.5, 5.0, 5.5, 6.0, 6.5, 7.0, 7.5, 8.0, 8.5, 9.0, 9.5, or 10 psi.

The length of the first layer 112 is shorter than the length of the second layer 114, such that when the first layer 112 and the second layer 114 overlap each other (as depicted in FIG. 1(a)), a lip 116 is created. Lip 116 can function as a physical access point for a user to de-couple or separate the first layer 112 from the second layer 114, such access point making it easier for the user to de-couple the first layer 112 from the second layer 114. Lip 116 can also be used as a location at which a user can grip the clipping device 100 between said user's fingers (as described later in this specification).

The length of the first layer 112 and second layer 114 can be any suitable length as long as both first layer 112 and second layer 114 are of a length that is longer than the width of the object (e.g. bulk packaging) that first component 110 is adapted to receive between first layer 112 and second layer 114.

In other embodiments, the first layer 112 and the second layer 114 are coupled together at edges 112c and 114c by another coupling mechanism known in the art. In other embodiments, the first layer 112 and second layer 114 are not coupled to each other at edges 112c and 114c. In other embodiments, first layer 112 and second layer 114 are not necessarily longer than the object received therebetween.

Figure 2A:
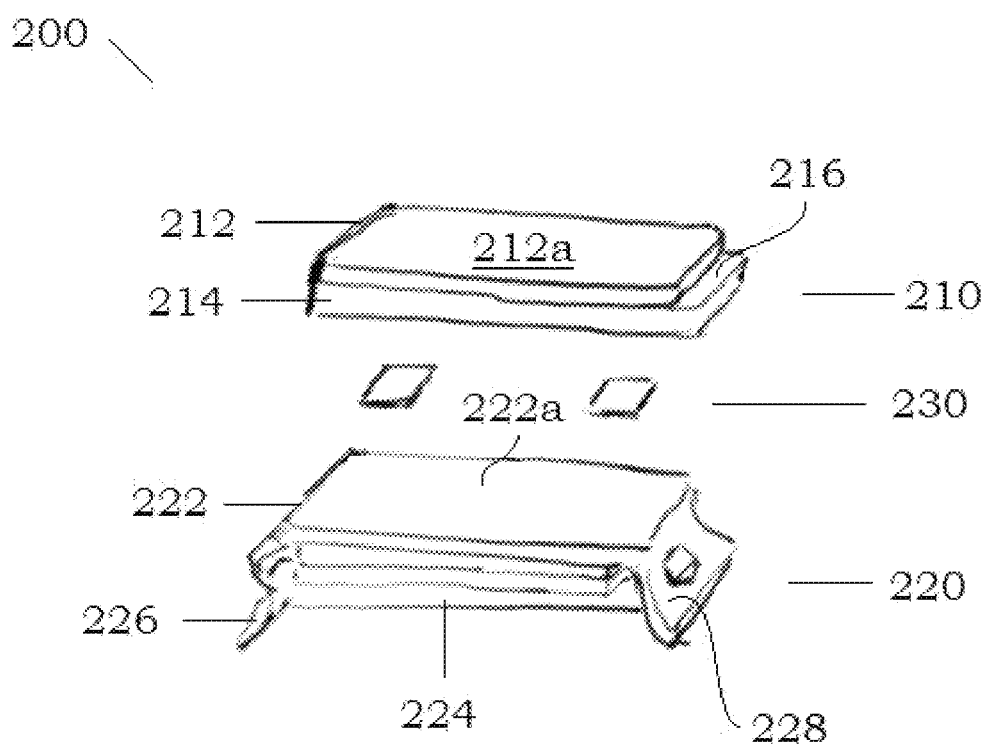
FIG. 2(a) is an exploded view of a clipping device, the clipping device comprising a first component, a second component, and a coupling means for coupling the first component and the second component together, the first component and the second component both being depicted in a "closed" position.
Figure 2B:
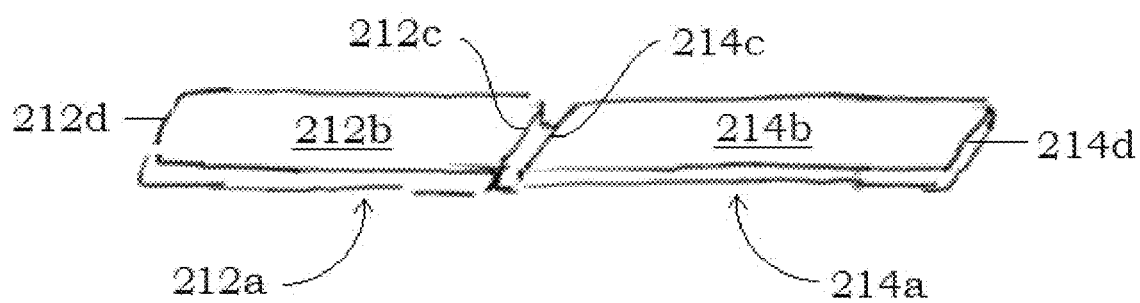
FIG. 2(b) is a perspective view of the first component of the clipping device depicted in FIG. 2(a), the first component being depicted in an "opened" position.
Figure 2C:
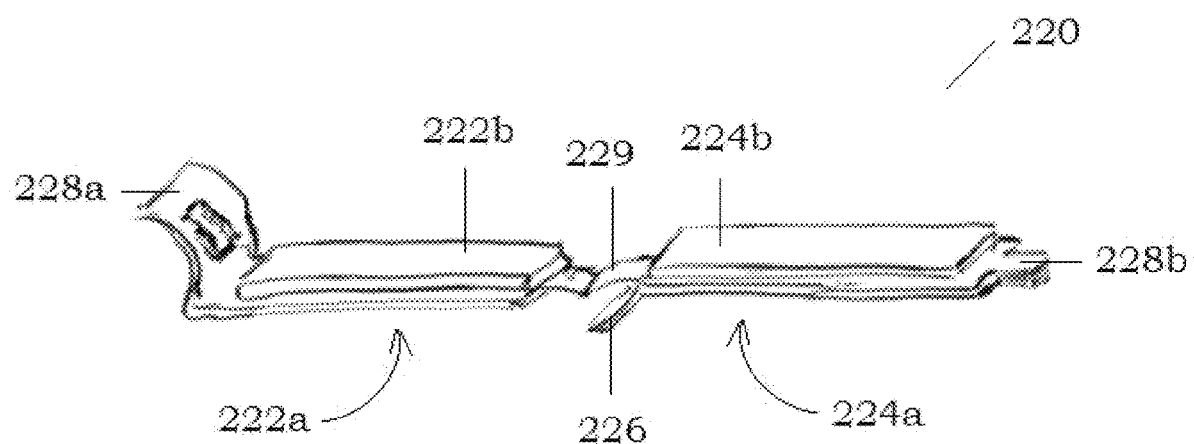
FIG. 2(c) is a perspective view of the second component of the clipping device depicted in FIG. 2(a), the second component being depicted in an "opened" position.

Referring to FIGS. 2(a) to 2(c), and according to another embodiment of a clipping device, there is a clipping device 200. The clipping device 200 comprises a first component 210, a second component 220, and a coupling means 230 for coupling first component 210 to second component 220.

First component 210 comprises a first layer 212 and a second layer 214. The first layer 212 comprises a first surface 212a, and a second surface 212b that is opposite the first surface 212a. The first layer 212 also comprises a first edge 212c and a second edge 212d that is opposite the first edge 212c. The second layer 214 comprises a first surface 214a, and a second surface 214b that is opposite the first surface 214a. The second layer 214 also comprises a first edge 214c and a second edge 214d that is opposite the first edge 214c. First layer 212 and second layer 214 are coupled to each other at edges 212c and 214c by a hinge mechanism, the hinge mechanism for permitting first layer 212 to overlap with second layer 214 and for allowing the first component 210 to reversibly transition from an "opened" position to a "closed" position.

The first layer 212 and the second layer 214 each comprise a magnetic material, such that an attractive magnetic force is created between the surface 212b and surface 214b when surface 212b and surface 214b are proximate to each other and arranged relative to each other in an overlapping manner. The magnetic material may be any suitable magnetic material known in the art such as but not limited to permanent magnets, temporary magnets, ceramic magnets, ferrite magnets, magnets comprising neodymium.

The first component 210 is adapted for receiving an object (e.g. an opened bulk package containing acupuncture needles therein) between surface 212b and surface 214b. As contemplated in this embodiment, first component 110 is adapted for receiving bulk packaged needles that are packaged in a pouch pack style. When the object is received between surface 212b and surface 214b, the attractive magnetic force created by placing surface 212b and surface 214b proximate to each other in overlapping arrangement restricts the ability of the object (and any other removable or loose articles therein or thereon) to move relative to the first component 210, but is not so strong so that any removable or loose articles (e.g. acupuncture needles) in or on the object (e.g. bulk packaging) cannot be removed from between surface 212b and surface 214b upon application of a pulling force that is applied substantially perpendicular to the direction of the attractive magnetic force between surface 212b and surface 214b. As contemplated in this embodiment, the attractive magnetic force created by placing surface 212b and surface 214b proximate to each other in overlapping arrangement correlates to a pressure on the object that ranges between about 0.7 psi and about 10 psi. For example, the pressure exerted on an object disposed between surface 212b and surface 214b as a result of the attractive magnetic force created by placing surface 212b and surface 214b can range from about 0.7 psi to about 8 psi, about 0.7 psi to about 6 psi, about 1.5 psi to about 5 psi, about 2 psi to about 4 psi. For example, the psi can be 0.7, 1.0, 1.2, 1.4, 1.6, 1.8, 2.0, 2.2, 2.4, 2.6, 2.8, 3.0, 3.5, 4.0, 4.5, 5.0, 5.5, 6.0, 6.5, 7.0, 7.5, 8.0, 8.5, 9.0, 9.5, or 10 psi.

The length of the first layer 212 is shorter than the length of the second layer 214, such that when the first layer 212 and the second layer 214 overlap each other (as depicted in FIG. 2(a)), a lip 216 is created. Lip 216 can function as a physical access point for a user to de-couple or separates the first layer 212 from the second layer 214, such physical access point making it easier for the user to de-couple the first layer 212 from the second layer 214. Lip 216 can also be used as a location at which a user can grip the first component 210 between said user's fingers (as described later in this specification).

The length of the first layer 212 and second layer 214 can be any suitable length as long as both first layer 212 and second layer 214 are of a length that is longer than the width of the object (e.g. bulk packaging) that first component 210 is adapted to receive between first layer 212 and second layer 214.

In other embodiments, the first layer 212 and the second layer 214 are coupled together at edges 212c and 214c by another coupling mechanism known in the art. In other embodiments, the first layer 212 and second layer 214 are not coupled to each other at edges 212c and 214c. In other embodiments, first layer 212 and second layer 214 are not necessarily longer than the object received therebetween.

The second component 220 comprises a first layer 222 and a second layer 224. The first layer 222 has a first surface 222a and a second surface 222b that is opposite the first surface 222a. The second layer 224 has a first surface 224a and a second surface 224b that is opposite the first surface 224a. The second surfaces 222b and 224b can be made of any suitable material that can provide a frictional grip against an object that is placed therebetween. As contemplated in this embodiment, the second surfaces 222b and 224b are made of a deformable material (e.g. a foam material).

First layer 222 and second layer 224 are coupled together by a means known in the art, and in a manner that allows the first layer 222 and the second layer 224 to overlap (and particularly second surface 222b and second surface 224b to overlap and face each other) and that allows the second component 220 to reversibly transition from an "opened" position to a "closed" position. As contemplated in this embodiment, such means is a hinge 229. In other embodiments, such means can be a functionally equivalent mechanism known in the art.

The second component 220 further comprises a locking mechanism 228 comprising a first part 228a and a second part 228b. First part 228a comprises an aperture (un-numbered) through which second part 228b is adapted to extend when the second surface 222b and second surface 224b to overlap and face each other and are brought sufficiently closer in proximity to one another to facilitate such extension of second part 228b through the aperture (un-numbered) of first part 228a. As contemplated in this embodiment, the edges of the aperture (un-numbered) of first part 228a are serrated and the sides of second part 228b are serrated such that when second part 228b extends through the aperture (un-numbered) of part 228a, the serrated edges of the aperture (un-numbered) of first part 228a and the serrated sides of second part 228b inter-lock so as to improve the couplability between first part 228a and a second part 228b. When the first part 228a and the second part 228b are not coupled together, the mechanism 228 is in an "unlocked" position. When the first part 228a and the second part 228b are coupled together, the mechanism 228 is in a "locked" position. In other embodiments, the edges of the aperture (un-numbered) of first part 228a and the sides of second part 228b have other suitable complementary formations that inter-lock so to improve couplability between a first part 228a and a second part 228b.

The second component 220 further comprises an extension 226 that extends in a direction that is away from the first surface 224a (though extension 226 does not necessarily extend from the first surface 224a). When the locking mechanism 228 is in a "locked" position, the locking mechanism 228 also forms an extension that extends in a direction that is away from the first surface 224a (though such extension does not necessarily extend from the first surface 224a), and together with extension 226 form a pair of "complementary supports" (e.g. legs) that are adapted to elevate first surface 224a above a surface on which the "complementary supports" may be adapted to rest.

The length of the first layer 222 and second layer 224 can be any suitable length as long as both first layer 222 and second layer 224 are of a length that is longer than the width of the object (e.g. bulk packaging) that second component 220 is adapted to receive between first layer 222 and second layer 224.

The second component 220 is adapted for receiving an object (e.g. an opened bulk package containing acupuncture needles therein) between surface 222b and surface 224b. When the object is received between surface 222b and surface 224b, a compressive force can be created between surface 222b and surface 224b as the surfaces are brought together in overlapping arrangement such that second part 228b can be inserted through the aperture (un-numbered) of first part 228a, and such that second part 228b and first part 228a inter-lock.

A length of the second part 228b extending through the aperture of the first part 228a is correlated to a magnitude of force exerted between the deformable materials of the first layer 222 and the second layer 224 of the second component 220, when such deformable materials overlap each other. That is, once first part 228a and second part 228b are inter-locked, the clamping force between surface 222b and surface 224b can be increased by pushing first part 228a in a direction towards extension 226.

The clamping force exerted between surface 222b and surface 224b restricts the ability of the object (and any other removable or loose articles therein or thereon) disposed between surface 222b and surface 224b to move relative to the second component 220, but is not so strong so that any removable or loose articles (e.g. acupuncture needles) in or on the object (e.g. bulk packaging) cannot be removed from between surface 222b and surface 224b upon application of a pulling force that is applied substantially perpendicular to the direction of the clamping force between surface 222b and surface 224b.

First component 210 and second component 220 can be coupled together by a coupling mechanism 230 that is disposed between first component 210 and second component 220. As contemplated in this embodiment, the coupling mechanism 230 is one or more magnets (i.e. any suitable magnetic material known in the art), and first component 210 and second component 220 are coupled together by magnetic attraction. As contemplated in this embodiment, coupling mechanism 230 is disposed on surface 222a. In other embodiments, coupling mechanism 230 can be disposed at another suitable location such as, but not limited to, under surface 222a. First component 210 and second component 220 are coupled together by the magnetic attractive force experienced between coupling mechanism 230 and the magnetic component of second layer 214 of first component 210. First component 210 and second component 220 may also be de-coupled from each other. In other embodiments, the coupling mechanism is any mechanism that is known in the art.

Figure 3A:
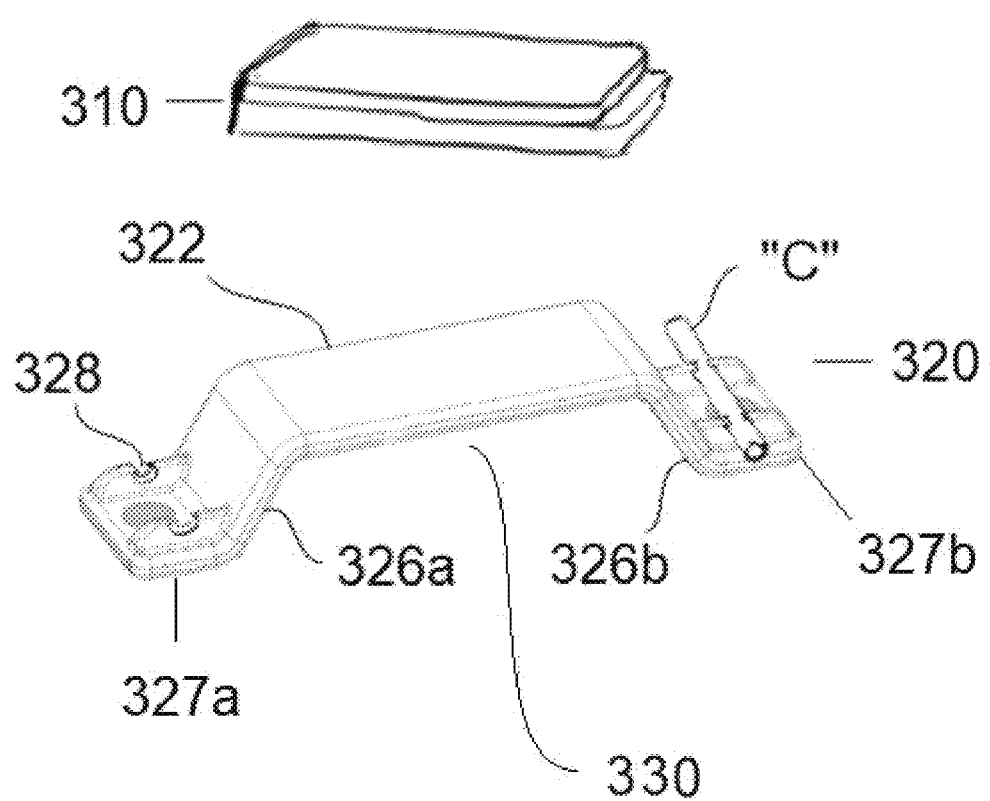
FIG. 3(a) is an exploded view of a clipping device, the clipping device comprising a first component and a second component. The first component is depicted in a "closed" position.
Figure 3B:
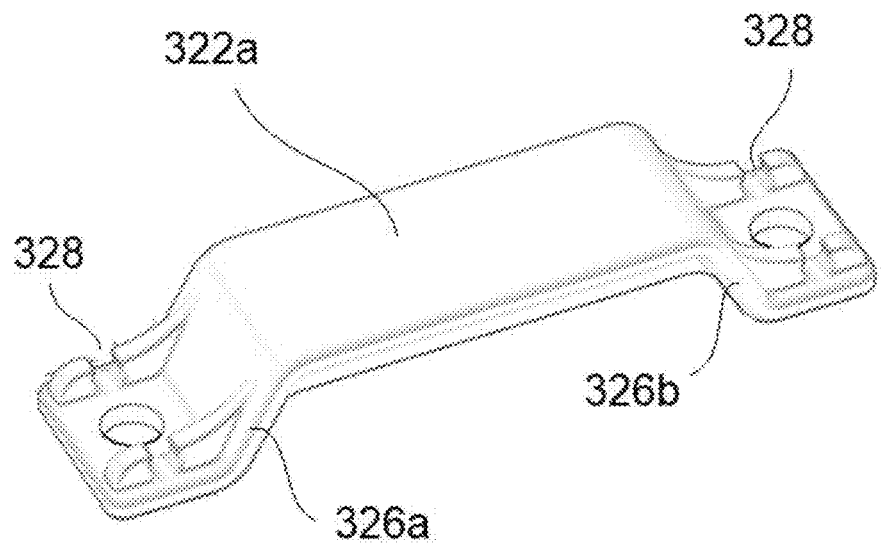
FIG. 3(b) is a first perspective view of the second component of the clipping device depicted in FIG. 3(a), the second component adapted for elevating one or more needles above a surface.
Figure 3C:
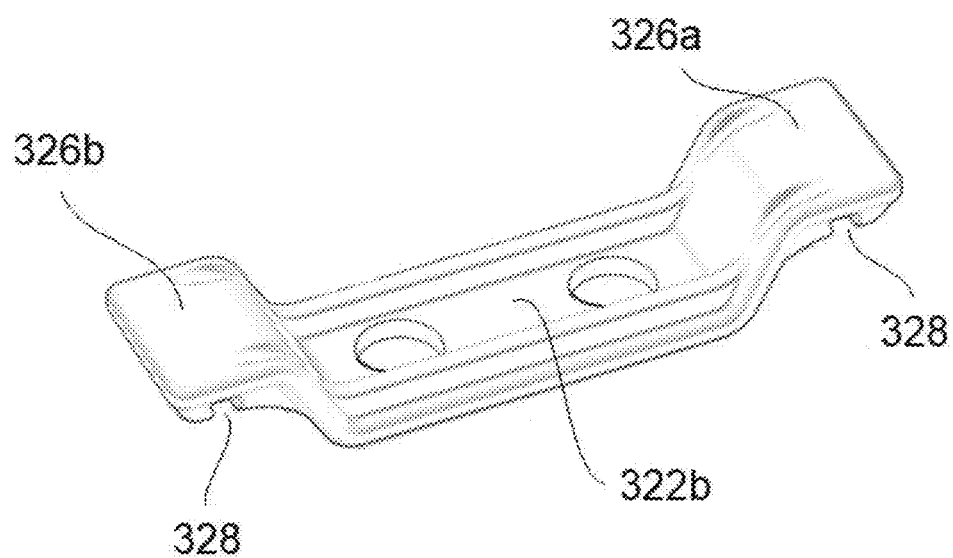
FIG. 3(c) is a second perspective view of the second component of the clipping device depicted in FIG. 3(a), the second component adapted for elevating one or more needles above a surface.

Referring to FIGS. 3(a) to 3(c), and according to another embodiment of a clipping device, there is a clipping device 300. The clipping device 300 comprises a first component 310, a second component 320, and a coupling means 330 for coupling first component 310 to second component 320.

First component 310 may be the same as or substantially similar to first component 110 or first component 210 as described above.

Second component 320 comprises a first portion 322. First portion 322 comprises a first surface 322a, and a second surface 322b that is opposite first surface 322a. Second component 320 further comprises a pair of arms 326a and 326b extending away from first portion 322, arms 326a and 326b being coupled to feet 327a and 328a respectively. Together, arm 326a and foot 327a form a first extension (not-numbered). Together, arm 326b and foot 327b form a second extension (not-numbered). The first extension and the second extension form a pair of "complementary supports" that are adapted to elevate first portion 322 above a surface on which the "complementary supports" may be adapted to rest (e.g. a table). Each foot 327a/327b further comprises a holder 328 configured to receive a longitudinal tube "C" (for example, a needle tube). Arms 326a and 326a and second surface 322b form a channel 330.

Second surface 322b comprises two depressions (un-numbered), each depression for receiving a magnet (not shown) therein. First component 310 can thereby be coupled to first surface 322a of second component 320 by magnetic attraction. In other embodiments, the second surface of the first portion of the second component comprises any suitable number of depressions, each for receiving a magnet therein. In other embodiments, the second surface of the first portion does not comprise any depressions.

In other embodiments, a magnetic layer is coupled to surface 322a and configured for direct contact with a first component 310.

Second component 320 is made of any suitable material. As contemplated in this embodiment, second component 320 is made of plastic.

Second component 320 serves as a supporting base to first component 310 and is configured to support the mass of first component 310. Alternatively, second component 320 serves as a mount onto which first component 310 can be mounted via magnetic attraction to second component 320.

Example Use of Clipping Device

Figure 4A:
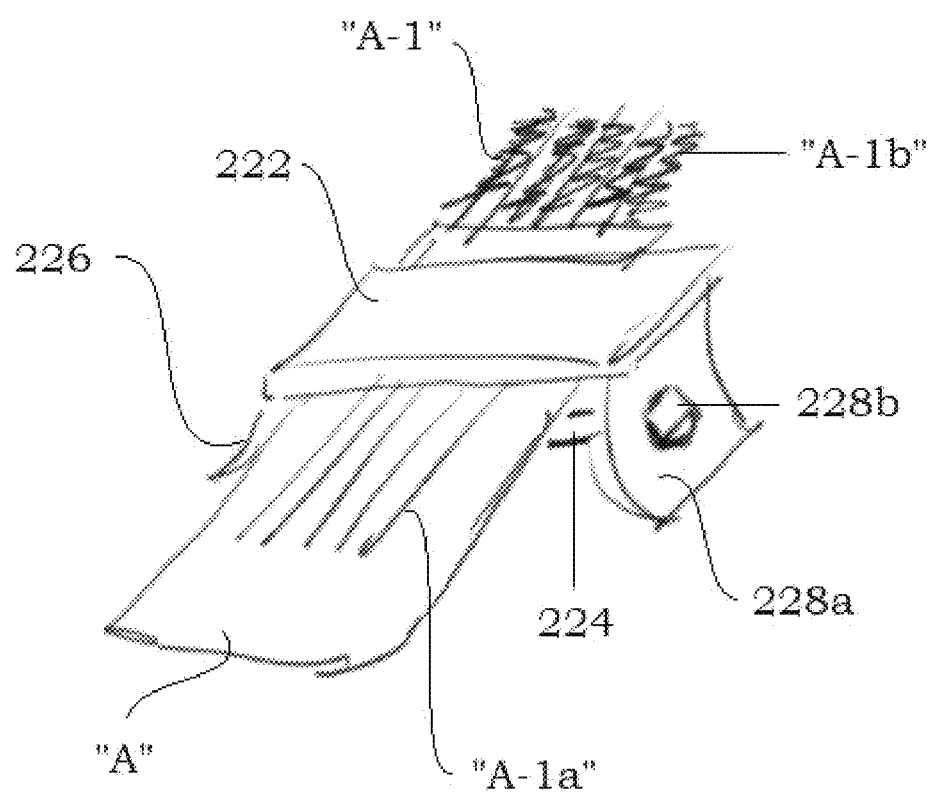
FIG. 4(a) is a perspective view of the second component of the clipping device depicted in FIG. 2(a), the second component being depicted in a "closed" position, an open package of acupuncture needles being disposed in between a first layer and a second layer of the second component.

Referring to FIG. 4(a), and using clipping device 200 as an example, an opened bulk package "A" (e.g. blister style package or pouch style package) with acupuncture needles "A-1" disposed therein is disposed between first layer 222 and second layer 224 (and specifically surfaces 222b and 224b) of second component 220. An acupuncture needle "A-1" comprises a shaft portion "A-1a" and a head portion "A-1b". The bulk package is positioned between surfaces 222b and 224b such that the shaft portions "A-1a" of the acupuncture needles (but note the head portions "A-1b") overlap with surfaces 222b and 224b when surfaces 222b and 224b overlap and face each other. The opened bulk package "A" is positioned between surfaces 222b and 224b such that when the locking mechanism 228 transitions from an "unlocked" position to a "locked" position, a compressive force is exerted against the shaft portions "A-1a" of the acupuncture needles "A-1" within the opened bulk package "A". When the locking mechanism 228 is in a "locked" position, a compressive force (as a result of bringing surfaces 222b and 224b proximate to each other in overlapping arrangement) remains exerted against the shafts "A-1a" of the acupuncture needles "A-1" disposed within the opened bulk package "A". The acupuncture needles "A-1" become sandwiched between surfaces 222b and 224b, and the compressive force exerted on the acupuncture needles "A-1" is sufficient to prevent movement of the opened bulk package "A" with acupuncture needles "A-1" disposed therein relative to surfaces 222b and 224b but is not so strong as to physically distort (e.g. crimp) the acupuncture needles "A-1" or to prevent removal of an acupuncture needle "A-1" from the opened bulk package "A" when a suitable pulling force (that is substantially perpendicular to the direction in which force is exerted on the opened bulk package "A" with acupuncture needles "A-1" disposed therein) is applied to said needle "A-1" at head portion "A-1b". Second component 220 elevates the opened bulk package "A" above a surface on which second component 220 rests, so as to decrease the likelihood of contamination to the opened bulk package and contents therein.

Figure 4B:
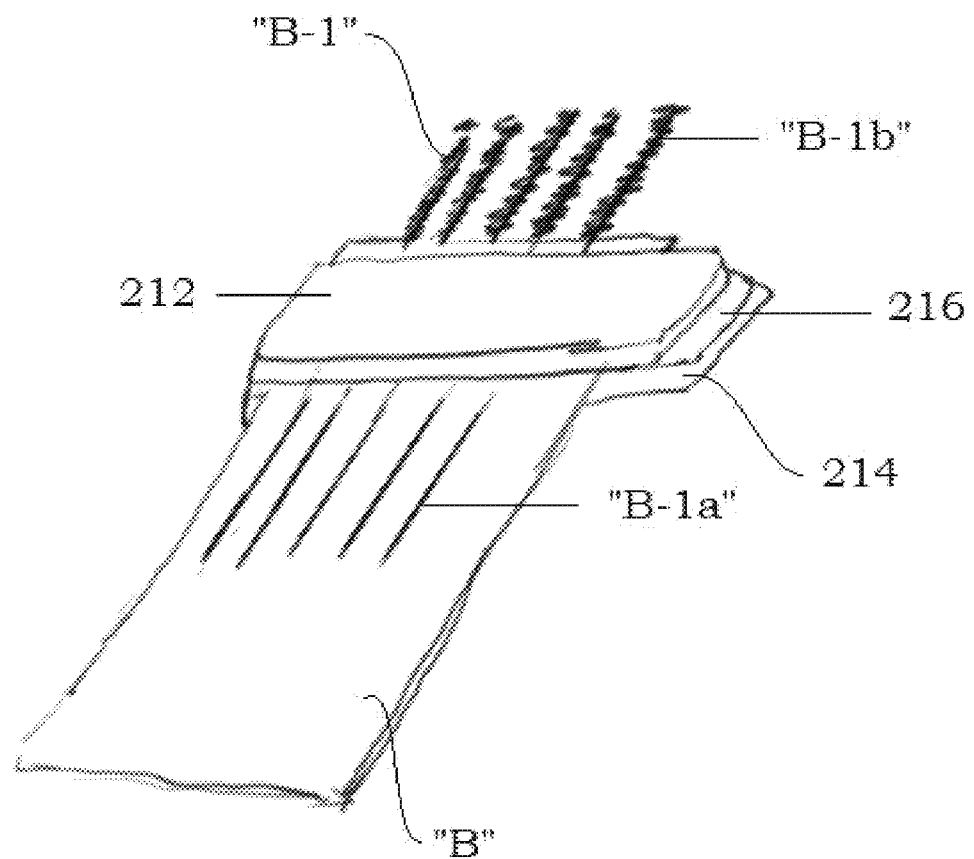
FIG. 4(b) is a perspective view of the first component of the clipping device depicted in FIG. 2(a), the first component being depicted in a "closed" position, an open package of acupuncture needles being disposed in between a first layer and a second layer of the first component.

Referring to FIG. 4(b), and using clipping device 200 as an example (note that clipping device 100 can also be used as a comparable example), an opened bulk package "B" with acupuncture needles "B-1" disposed therein is disposed between surfaces 212b and 214b of first component 210. An acupuncture needle "B-1" comprises a shaft portion "B-1a" and a head portion "B-1b". The bulk package "B" is positioned between surfaces 212b and 214b such that the shaft portions "B-1a" of the acupuncture needles "B-1" overlap with surfaces 212b and 214b when surfaces 212b and 214b over and face each other. The opened bulk package "B" is positioned between surfaces 212b and 214b such that when an attractive magnetic force is created between surfaces 212b and 214b (thereby holding surfaces 212b and 214b in position relative to each other), a force is exerted against the shaft portions "B-1a" of the acupuncture needles "B-1" within the opened bulk package "B". At such point, the acupuncture needles "B-1" become "sandwiched" between surfaces 212b and 214b, and the attractive magnetic force created between surfaces 212b and 214b is sufficient to prevent movement of the opened bulk package "B" with acupuncture needles "B-1" disposed therein relative to surfaces 212b and 214b but not so strong as to physically distort (e.g. crimp) the acupuncture needles "B-1" or to prevent removal of an acupuncture needle "B-1" from the opened bulk package "B" when a suitable pulling force (that is substantially perpendicular to the direction in which the attractive magnetic force is exerted on the opened bulk package "B" with acupuncture needles "B-1" disposed therein) is applied to said needle "B-1" at head portion "B-1b".

Figure 4C:
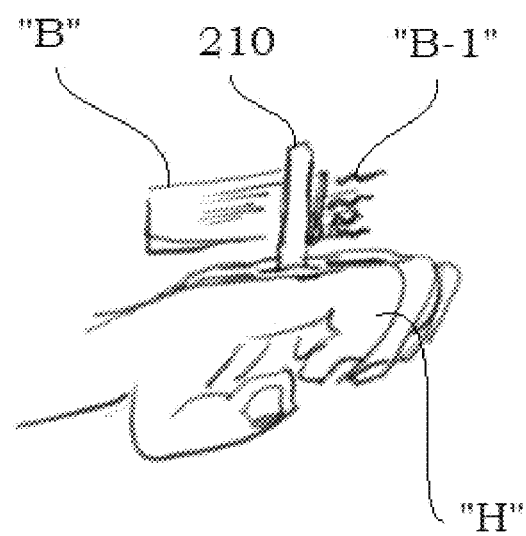
FIG. 4(c) is a side view the first component of the clipping device depicted in FIG. 2(a), the first component being depicted in a "closed" position, an open package of acupuncture needles being disposed in between a first layer and a second layer of the first component, the first component being held by a user.

Referring to FIG. 4(c), and using first component 210 as an example (note that first component 110 can also be used as a comparable example), first component 210 can be hand held by a user at or around lip 216 such that the first component 210 extends in a direction that is substantially perpendicular to at least a portion of the hand "H" of the user. Because acupuncture needles "B-1" are arranged in a direction that is substantially perpendicular to the first component 210, a user is given the ability to draw (through a pulling force exerted on a head portion "B-1b" of a desired acupuncture needle "B-1") the acupuncture needles "B-1" one-by-one from the bulk package "B", without having to touch another needle "B-1" within the same packaging.

Figure 4D:
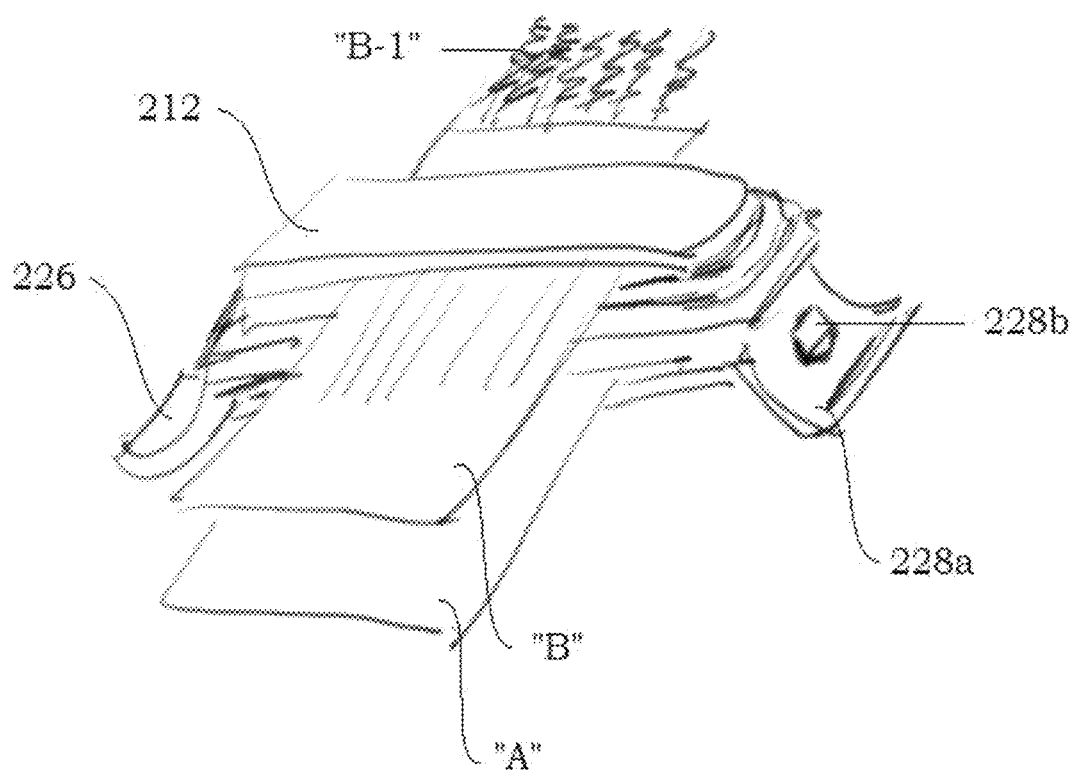
FIG. 4(d) is a perspective view of the clipping device depicted in FIG. 2(a), an open package of acupuncture needles being disposed in between a first layer and a second layer of the first component, an open package of acupuncture needles being disposed in between a first layer and a second layer of the second component.

Referring to FIG. 4(d), first component 210 is couplable to second component 220. Multiple packages of acupuncture needles can be arranged ready for use by a user, and the acupuncture needles can be arranged in positions that are ready for removal from the packaging one-by-one when required by the user. In some uses, first component 210 and second component 220 are de-coupled. In some uses, second component 220 rests on a surface and surface 224a is elevated above such surface by the "complementary legs" formed by extension 226 and locking mechanism 228 in a "locked" position. As contemplated in this example, first component 210 is adapted for receiving pouch style packaging. As contemplated in this example, second component 220 is adapted for receiving pouch style packaging, blister style packaging, and needle insertion tubes.

GENERAL

It is contemplated that any part of any aspect or embodiment discussed in this specification may be implemented or combined with any part of any other aspect or embodiment discussed in this specification. While particular embodiments have been described in the foregoing, it is to be understood that other embodiments are possible and are intended to be included herein. It will be clear to any person skilled in the art that modification of and adjustment to the foregoing embodiments, not shown, is possible.

Unless defined otherwise, all technical and scientific terms used herein have the same meaning as is commonly understood by one of ordinary skill in the art to which this invention belongs. In addition, any citation of references herein is not to be construed nor considered as an admission that such references are prior art to the present invention.

The scope of the claims should not be limited by the example embodiments set forth herein, but should be given the broadest interpretation consistent with the description as a whole.

What is claimed is:

1. A supporting base comprising:
    (a) a first portion comprising a first surface and a second surface that is opposite the first surface, the first portion further comprising a plurality of edges circumscribing at least the first surface, the plurality of edges including a first edge and a second edge that is opposite the first edge;
    (b) a magnetic layer coupled to the first surface of the first portion;
    (c) a first support extending away from the first edge, the first support comprising a portion that serves as a first foot;
    (d) a second support extending away from the second edge, the second support comprising a portion that serves as a second foot;
        wherein the first support, the second support, and the second surface of the first portion form a channel;
        wherein the magnetic layer coupled to the first surface of the first portion is configured to couple to a first component through magnetic attraction; and
        wherein the supporting base is configured to support a mass of the first component.

2. The supporting base as claimed in claim 1, wherein the first foot comprises a holder that is configured to receive a longitudinal tube.

3. The supporting base as claimed in claim 1, wherein the magnetic layer is selected from a group consisting of ceramic magnets, ferrite magnets, magnets comprising neodymium, and any combination thereof.

4. A device comprising:
(a) the supporting base as claimed in claim 1; and
(b) the first component, the first component comprising:
- (i) a first layer comprising a first surface and a second surface opposite the first surface, the second surface comprising a first magnetic material;
- (ii) a second layer comprising a first surface and a second surface opposite the first surface, the second surface comprising a second magnetic material;

the second magnetic material of the first component and the magnetic layer of the supporting base being configured to create an attractive magnetic force therebetween when the second magnetic material of the first component and the magnetic layer of the supporting base are proximate to each other and in an overlapping arrangement.

5. The device as claimed in claim 4, wherein the first layer and the second layer of the first component are coupled to each other in a manner to permit the first component to reversibly transition between an opened position and a closed position.

6. The device as claimed in claim 4, wherein the first magnetic material is selected from a group consisting of ceramic magnets, ferrite magnets, magnets comprising neodymium, and any combination thereof.

7. The device as claimed in claim 4, wherein the second magnetic material is selected from a group consisting of ceramic magnets, ferrite magnets, magnets comprising neodymium, and any combination thereof.

8. The device as claimed in claim 4, wherein the second layer is longer than the first layer such that when the first layer overlaps with the second layer, a lip is created.

\* \* \* \* \*